(12) United States Patent
Rucinski

(10) Patent No.: US 7,959,617 B2
(45) Date of Patent: Jun. 14, 2011

(54) DEVICES AND METHODS FOR DELIVERING ACTIVE AGENTS TO TARGET SITES

(75) Inventor: Paul J. Rucinski, Gainesville, FL (US)

(73) Assignee: Innovation Technologies, Inc., Gainesville, FL (US)

( * ) Notice: Subject to any disclaimer, the term of this patent is extended or adjusted under 35 U.S.C. 154(b) by 0 days.

(21) Appl. No.: 12/605,676

(22) Filed: Oct. 26, 2009

(65) Prior Publication Data

US 2010/0049149 A1 Feb. 25, 2010

Related U.S. Application Data

(63) Continuation of application No. 11/960,390, filed on Dec. 19, 2007, now Pat. No. 7,662,125.

(60) Provisional application No. 60/875,788, filed on Dec. 19, 2006.

(51) Int. Cl.
*A61M 35/00* (2006.01)
*A61K 9/12* (2006.01)

(52) U.S. Cl. .......................... 604/310; 424/45
(58) Field of Classification Search .................. 604/19
See application file for complete search history.

(56) References Cited

U.S. PATENT DOCUMENTS

| 2005/0113794 | A1 | 5/2005 | Rucinski | |
|---|---|---|---|---|
| 2005/0148958 | A1* | 7/2005 | Rucinski | 604/290 |
| 2005/0191247 | A1 | 9/2005 | Drake et al. | |
| 2007/0184114 | A1* | 8/2007 | Cevc | 424/484 |

FOREIGN PATENT DOCUMENTS

| WO | WO 02/07799 | 1/2002 |
|---|---|---|
| WO | WO 2007/070861 | 6/2007 |

OTHER PUBLICATIONS

Yu, H.Y.H., et al. "Chlorhexidine for Irrigation of Vas: a Clinical Trial and the Study of Viability of Non-Motile Sperms in Post-Vasectomy Patients with Trypan Blue Uptake," *Bristish Journal of Urology*, 1976, pp. 371-375, vol. 48.
Anderson, Maxwell H., "A Review of the Efficacy of Chlorhexidine on Dental Caries and the Caries Infection," *Journal of the California Dental Association*, Mar. 2003.
Demling, Robert H. and Waterhouse, Barbara, "The Increasing Problem of Wound Bacterial Burden and Infection in Acute and Chronic Soft-Tissue Wounds Caused by Methicillin-Resistant *Staphylococcus aureus*," *Journal of Burns and Wounds*, Nov. 2007, vol. 7, pp. 86-98.
MacNeill, S. et al., "Effects of tetracycline hydrochloride and chlorhexidine gluconate on *Candida albicans*: An in vitro study," *Journal of Clinical Periodontology*, Jan. 1997, vol. 24, pp. 753-760.
O'Grady, Naomi P. et al., "Guidelines for the Prevention of Intravascular Catheter-Related Infections," *Morbidity and Mortality Weekly Report*, Aug. 2002, vol. 51, No. RR10, pp. 1-26.
Puryan, Kenan et al., "Chlorhexidine Gluconate: An Ideal Scolicidal Agent in the Treatment of Intraperitoneal Hydatidosis?" *World Journal of Surgery*, Feb. 2005, vol. 29, No. 2, pp. 227-230.
Rahman, M. Rezanur et al., "Trial of chlorhexidine gluconate for fungal corneal ulcers," *Ophthalmic Epidemiology*, Sep. 1997, vol. 4, No. 3, pp. 141-149.
Regulatory Resources Group, Inc., "Traditional 510(k): IRRIMAX Corporation's IRRISEPT™ Wound Cleansing System," Mar. 19, 2008, application for FDA approval.
Xuguang, Sun et al., "Pharmacokinetics of Chlorhexidine Gluconate 0.02% in the Rabbit Cornea," *Journal of Ocular Pharmacology and Therapeutics*, 2006, vol. 22, No. 4, pp. 227-230.

* cited by examiner

*Primary Examiner* — Nicholas D Lucchesi
*Assistant Examiner* — Jason Flick
(74) *Attorney, Agent, or Firm* — Saliwanchik, Lloyd & Saliwanchik

(57) ABSTRACT

The subject invention provides novel, inexpensive, and highly effective methods and devices for convenient and effective wound irrigation. In one embodiment the subject invention provides a discharge means for a reservoir housing containing irrigation solution wherein the discharge means has one or more specifically designed nozzles through which a sufficient volume of the irrigation solution can pass at an appropriate pressure.

8 Claims, 3 Drawing Sheets

DEVICES AND METHODS FOR DELIVERING ACTIVE AGENTS TO TARGET SITES

CROSS-REFERENCE TO A RELATED APPLICATION

This application is a continuation application of application Ser. No. 11/960,390, filed Dec. 19, 2007 now U.S. Pat. No. 7,662,125; which claims the benefit of U.S. provisional application Ser. No. 60/875,788, filed Dec. 19, 2006, which are hereby incorporated by reference in their entirety.

BACKGROUND OF THE INVENTION

One of the great challenges in the health care profession is delivering drugs and other therapeutic agents to the site(s) where their activity is needed. Thus, there are many therapeutic agents whose usefulness is compromised because current methods of delivery and administration do not result in optimal presentation of the agent to the site(s) where its activity would be most beneficial.

There is a wide variety of options for administering therapeutic agents to a patient. Each route of administration poses unique challenges. These challenges include formulating the active agent in a physiologically-acceptable carrier, directing the agent to the appropriate site, delivering a concentration and amount of active agent that is effective and not toxic, and avoiding degradation of the agent such as that which occurs when an agent is administered systemically and is exposed to enzymes, the immune system and various metabolic processes.

One particularly challenging environment for delivering active ingredients is to the site of wounds, surgical sites, and other tissue openings. These sites often require the administration of active ingredients of a nature and at a concentration that is difficult, if not impossible, to achieve utilizing systemic routes such as oral and intravenous administration. Thus, direct administration of an active ingredient is often desirable yet such direct administration using previously-known techniques faces formidable challenges in terms of delivering active agents to the specific tissues and cells where the beneficial activities are most needed. In this regard, it should be noted that traditional methods of wound irrigation have not typically been combined with contemporaneous drug delivery.

In the management and treatment of a wound there are three primary objectives: (1) prevention of infection, (2) preservation and/or restoration of function, and (3) preservation and/or restoration of cosmetic appearance. The most important of these objectives is the prevention of infection. Success in the prevention of infection directly affects the healing process and the degree to which function and cosmetic appearance can be preserved and/or restored. However, heretofore, wound irrigation has not been directly combined with the administration of drugs that can reduce infection or otherwise promote healing.

It is known that the number of bacteria is a critical determinant of whether a wound becomes infected. Experimental evidence suggests that a critical level of bacteria is approximately $10^5$ organisms per gram of tissue. Below this level, wounds typically heal; at levels greater than $10^5$ bacteria per gram of tissue, wounds often become infected. All traumatic wounds are contaminated by the time the wound is presented to a medical care facility for treatment (Dire, Daniel I. [1990] "A comparison of Wound Irrigation Solutions Used in the Emergency Department," *Annals of Emergency Medicine* 19(6):704-708). Dirty wounds, or those that have not been treated within six hours, are likely to be contaminated with bacteria at levels that are higher than the critical level. Reducing the number of bacteria in and around the wound is critical for avoiding infection and expediting wound healing.

Methicillin-resistant *Staphylococcus aureus* (MRSA) infection is caused by *Staphylococcus aureus* bacteria—often called "staph." Decades ago, strains of staph emerged in hospitals that were resistant to the broad-spectrum antibiotics commonly used to treat them. These antibiotics include methicillin and other more common antibiotics such as oxacillin, penicillin and amoxicillin. Dubbed methicillin-resistant *Staphylococcus aureus* (MRSA), it was one of the first germs to be resistant to all but the most powerful drugs.

Staph bacteria are generally harmless unless they enter the body through a cut or other wound. In older adults and people who are ill or have weakened immune systems, ordinary staph infections can cause serious illness. Staph infections, including MRSA, occur most frequently among persons in hospitals and healthcare facilities, such as nursing homes and dialysis centers, who have weakened immune systems.

In the 1990s, a type of MRSA began appearing in the wider community. Today, that form of staph, known as community-associated MRSA, or CA-MRSA, is responsible for many serious skin and soft tissue infections and for a serious form of pneumonia. When not treated properly, MRSA infection can be fatal.

MRSA infections are spreading rapidly in the United States and worldwide. According to the Center for Disease Control and Prevention (CDC), the proportion of infections that are antimicrobial resistant has been growing. In 1974, MRSA infections accounted for two percent of the total number of staph infections; in 1995 it was 22%; and in 2004 it was nearly 63%. Additionally, recent research has suggested that 30-50% of the population carries MRSA colonies on their bodies all the time, helping to facilitate the spread of infection.

Although MRSA has traditionally been seen as a hospital-associated infection, there has also been an epidemic of CA-MRSA in the United States. MRSA infections in the community are usually manifested as skin infections, such as pimples and boils. These CA-MRSA infections can occur in otherwise healthy people, and commonly occur among athletes who share equipment or personal items including towels and razors. In fact, from 2000 to present, there have been several reported outbreaks of CA-MRSA affecting high school athletic teams. This epidemic among athletes is aided by the fact that MRSA grows very rapidly in warm, moist areas such as gyms and gym locker rooms. Common cuts and abrasions such as those frequently in football and baseball now pose significant threats due to the possibility of an MRSA infection.

Vancomycin is one of the few antibiotics still effective against hospital strains of MRSA infection, although the drug is no longer effective in every case. Several drugs continue to work against CA-MRSA, but CA-MRSA is a rapidly evolving bacterium, and it may be a matter of time before it, too, becomes resistant to most antibiotics.

Different procedures of wound management have been developed to help decrease the level of bacteria present in a wound, i.e., reduce the incidence of infection. The cleansing of a wound and the site surrounding the wound to remove blood clots, debris, dirt, or other foreign materials that can introduce contaminants, including pathogenic microorganisms, is critical in reducing levels of bacteria in and around the wound. There are numerous wound cleansing procedures presently used by healthcare professionals such as debridement, excision and irrigation. See, for example, Sinkinson, Craig Alan, ed. (1989) "Maximizing A Wound's Potential For Healing," *Emergency Medicine Reports* 10(11):83-89; Lammers, Richard L. (1991) "Soft Tissue Procedures: Principles of Wound Management," in *Clinical Procedures in Emergency Medicine*, Roberts and Hedges, eds., 2nd Ed., W.B. Saunders Company, pp. 515-521; Cracroft, Davis (1987) "Minor Lacerations and Abrasions," *Emergency Medicine: A Comprehensive Review*, Kravis and Warner, eds., 2nd cd., Aspen Publishing Co., pp. 107-110; and Mulliken, John B. (1984) "Management of Wounds," in *Emergency Medicine*, May ed., John Wiley & Sons, pp. 283-286.

Irrigation is the most commonly used procedure for cleansing of open contaminated wounds. Irrigation involves the application of sterile fluids to wounds to remove loose devitalized tissue, bacterial inoculum, blood clots, loose debris, and foreign bodies proximate to and within the depths of the wound. Two critical components of any effective wound irrigation method and/or device are: (1) the application of an adequate volume of sterile irrigation solution to the wound, and (2) the use of sufficient pressure applied in an effective dispersal pattern in the delivery of the solution to effectively remove contaminants. Regarding volume, the amount of irrigation solution required will depend upon the type of wound and the level of contamination. Injuries which can introduce a high amount of bacteria into a wound (such as puncture wounds and bites) may require 1 liter or more of irrigation solution.

U.S. Pat. No. 5,071,104 describes a wound irrigation apparatus and process for cleansing wounds which includes a pressure bladder, e.g, a blood pressure cuff, disposed proximate a reservoir holding a cleaning solution. The device in the '104 patent also includes a flexible tubular conduit for transmitting the solution from the reservoir to a single nozzle. The conduit and reservoir form a two-part system which is time consuming to set up, inconvenient to use, and costly.

U.S. Pat. No. 5,133,701 describes a disposable pressurized wound irrigation device which has a pressurized chamber for providing a force upon the reservoir such that a single liquid stream of cleansing solution is expelled from the device at a constant pressure. A propellant is used in evacuating the cleanser contents of the device. This invention requires a propellant and involves a relatively elaborate manufacturing and filling process which is labor intensive and requires specialized machinery. This device is also inconvenient to use and costly.

More recently, an advantageous wound irrigation system has been developed whereby a dispersed stream of irrigation fluid is easily and effectively applied to wounds. This system is described at, for example, U.S. Pat. Nos. 5,830,197 and 6,468,253 and International Patent Applications WO 00/15279 and WO 02/007799. These disclosures are incorporated herein by reference, in their entirety.

Chlorhexidine is a chemical antiseptic, and it combats both gram positive and gram negative microbes. It is bacteriostatic, hampering the growth of bacteria, and bacteriocidal, killing bacteria. It is often used as an active ingredient in mouthwash designed to kill dental plaque and other oral bacteria. Chlorhexidine also has non-dental applications, though. It is used for general skin cleansing, as a surgical scrub, and as a preoperative skin preparation.

Chlorhexidine is typically used in the form of acetate, gluconate, or hydrochloride, either alone or in combination with other antiseptics such as cetrimide. It can be deactivated by anionic compounds, including the anionic surfactants commonly used as detergents in toothpastes and mouthwashes.

BRIEF SUMMARY OF THE INVENTION

The subject invention provides novel and highly effective methods and devices for efficient delivery of one or more medications or other active ingredients to a target site in a patient.

In one embodiment, the subject invention provides a reservoir housing containing an irrigation solution with one or more active agents, wherein the reservoir housing has attached to it a discharge means having a plurality of ports through which a sufficient volume of the solution can pass at an appropriate pressure for effective delivery of the solution, including the active agent, to a target site.

Examples of agents that can be administered to a patient in accordance with the subject invention include, but are not limited to, bacterial agents, anti-viral agents, fungicidal agents, chemotherapy agents, topical antiseptics, anesthetic agents, oxygenated fluids and/or agents, antibiotics, diagnostic agents, homeopathic agents, and over the counter medications/agents. In a preferred embodiment, the active agent is chlorhexidine gluconate, preferably at a concentration of less than 0.05%.

In a preferred embodiment, the reservoir housing, upon which the discharge means is either permanently or detachably affixed, is compressible (e.g., plastic bottles in which saline solutions are presently available). The operator (i.e., medical or health care professional or other person) using the subject device and providing therapy can easily compress the reservoir housing to force the solution through the nozzles of the discharge means under sufficient pressure to effectively deliver the active agent to a target site and, preferably, to dislodge contaminants including bacteria and debris.

In a preferred embodiment, the bottle is constructed to quickly return to its original shape once compression is finished. Thus, the bottle is quickly ready for another compression.

The subject invention provides an easy to use, economical drug delivery system that is capable of delivering adequate volumes of solution (without refilling the reservoir) and active drug ingredient in a dispersed stream under sufficient pressure to effectively deliver the active agent to a target site.

DETAILED DESCRIPTION OF THE INVENTION

Figure 1:
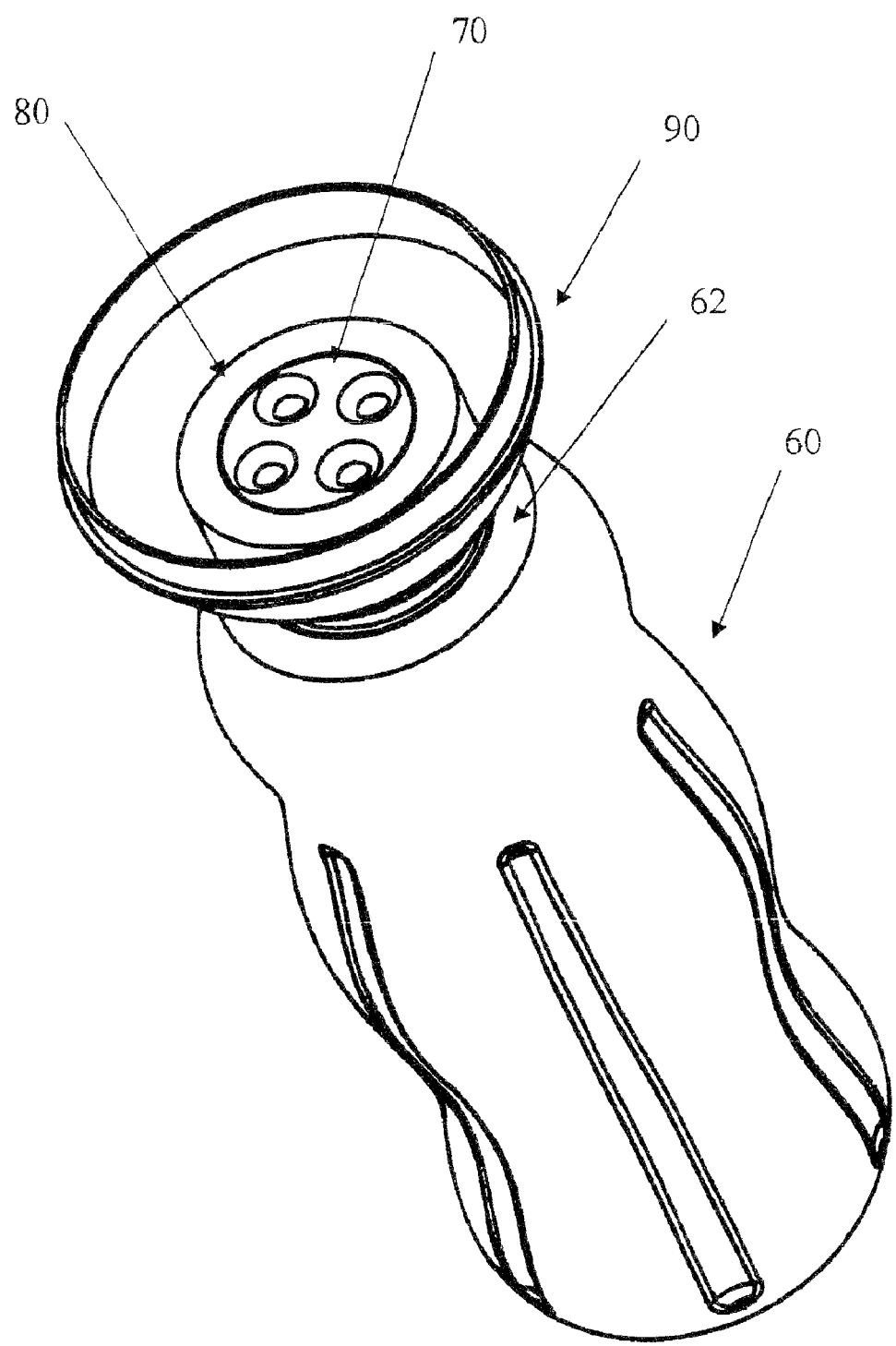
FIG. 1 shows one embodiment of the device of the subject invention.
Figure 2C:
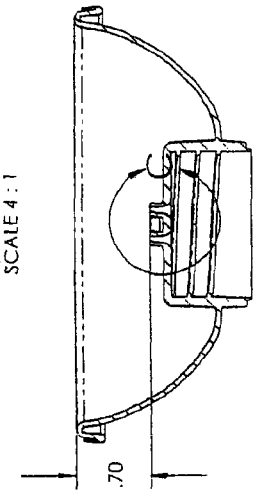
FIG. 2 shows embodiments of the ports of the subject invention.
Figure 2D:
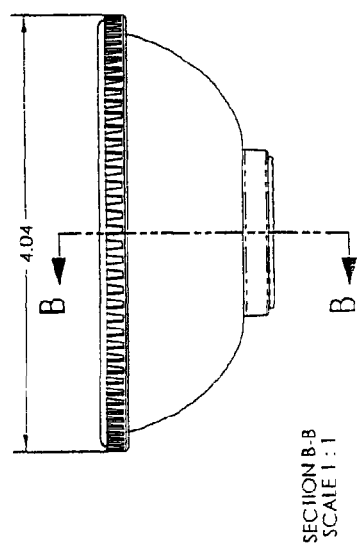
Figure 2A:
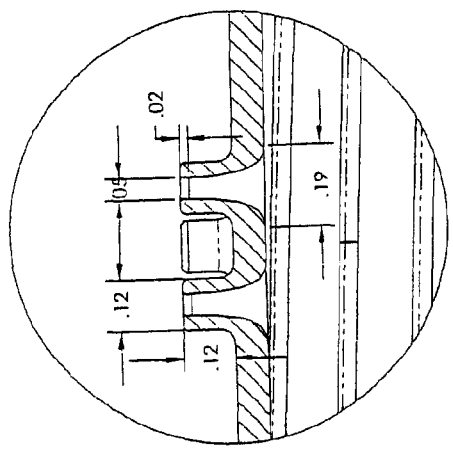
Figure 2B:
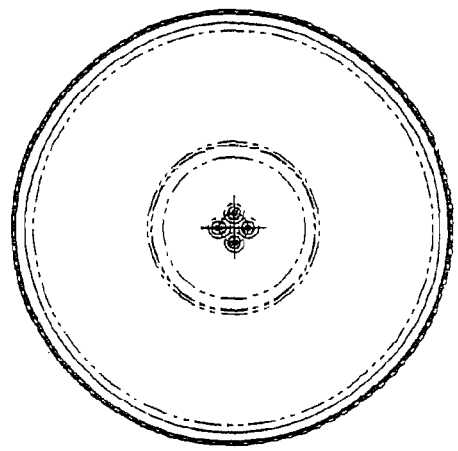

The subject invention provides novel, convenient, inexpensive, and effective drug delivery devices that comprise, in a preferred embodiment, a reservoir housing and a discharge means having a plurality of nozzles for delivering an active agent to a target site. The subject invention also provides methods of use for the device.

The materials and methods of the subject invention make it possible to conveniently and easily apply a stream of fluid containing for example, a medicinal agent to, for example, a wound, with the stream having an appropriate volume, pressure, and dispersal pattern.

As used herein, "active agents" refers to compounds or other entities that perform a therapeutic and/or diagnostic function. This function may be direct, such as promoting tissue repair or killing cancer cells, or may be indirect by eliciting a physiological response that ultimately results in the desired beneficial result.

In a preferred embodiment, a sterile water (not saline) solution comprising 0.05% or less (or even less than 0.04% or even less than 0.03%) of chlorhexidine is applied to a wound in the skin of a human. Preferably the wound is then rinsed within five minutes (preferably within 1-3 minutes) with a sterile saline or water liquid that does not contain chlorhexidine.

In a specific embodiment, the chlorhexidine gluconate used according to the subject invention has the following chemical structure:

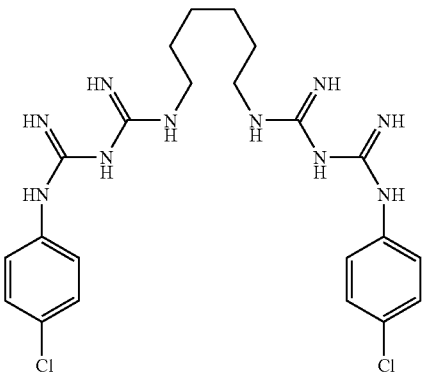

Chlorhexidine Gluconate

| | |
|---|---|
| Systematic (IUPAC) Name | 1-[amino-[6-[amino-[amino-(4-chlorophenyl)amino-methylidene]amino-methylidene]aminohexylimino]methyl]imino-N-(4-chlorophenyl)-methanediamine |
| Chemical Data | |
| Formula | $C_{22}H_{30}Cl_2N_{10}$ |
| Mol. weight | 505.446 g/mol |

In a preferred embodiment, about 15-25 mg of chlorhexidine gluconate is applied to a wound. In a further preferred embodiment, the wound is an abrasion or laceration and the solution is applied prior to repair/closure.

Preferably, the pH of the solution is neutral or slightly acidic. Preferably the pH is 5.0 to 7.5. More preferably the pH is 5.5. to 7.0. In one embodiment, the chlorhexidine is applied without a sudsing agent.

In a preferred embodiment, the application of the irrigated solution of the subject invention results in a reduction in the number of bacteria at the wound when compared to either an untreated wound or a wound irrigation with saline that does not contain chlorhexidine.

Advantageously, the irrigation solution of the subject invention is effective in combating infection, even when organic materials (including blood, desired tissue, and/or dirt and debris) are present. Of course, such materials are present in all skin wounds.

In addition to killing bacteria, the formulations of the subject invention can also "depathogenize" certain bacteria including, for example, *E. coli* and *Klebsiella aerogenes*, making these bacteria less able to cause infection.

The drug delivery methods of the subject invention can be used in conjunction with the delivery of an active agent by many of the routes set forth in Table 1. Of particular interest are: buccal, conjunctival, cutaneous, dental, intra-abdominal, intralesional, intraocular, intrathoracic (during surgery), irrigation, nasal, ophthalmic, periodontal, rectal, soft tissue, subcutaneous, topical, and vaginal routes.

Under optimal circumstances, the drug delivery devices and methods of the subject invention are utilized by trained medical technicians; however, because of the simplicity and convenience of the devices of the subject invention, they can be used to greatly enhance the effectiveness of drug delivery regardless of the training level of the operator performing the irrigation.

Delivering Active Agents

Examples of agents that can be administered to a patient in accordance with the subject invention include, but are not limited to, bacterial agents, anti-viral agents, fungicidal agents, chemotherapy agents, topical antiseptics, anesthetic agents, oxygenated fluids and/or agents, antibiotics, diagnostic agents, homeopathic agents, and over the counter medications/agents.

The target sites to which an active ingredient can be administered according to the subject invention include, but are not limited to, wounds, the eyes, and surgical sites. The surgical sites may include, for example, joint replacements, abdominal surgery and oral/periodontal surgery sites. In each case, the ability to deliver the active agent to a specific site, at an appropriate dosage, at a carefully controlled pressure, is unique and highly advantageous.

The solution that carries the active agent can be, for example, water, saline, or a balanced salt solution. The solution is preferably sterile. The device can be sterilized by known sterilization techniques, including boiling, autoclaving, gas sterilization and the like, either separately or together with the reservoir housing.

Buffered Ringer's solution or commercially available balanced salt solution (e.g., Tis-U-Sol or Physio-Sol) are physiologically compatible and are commonly used in wound irrigation procedures.

The antiseptic agents most commonly used in wound care at present include:

Povidone-iodine solution (Betadine preparation)-iodine added to the carrier polyvinylpyrrolidone (PVP), a water-soluble organic complex; this combination is called an iodophor. Standard solutions of Betadine preparation are 10 percent.

Povidone-iodine surgical scrub (Betadine scrub)—the iodophor PVP-I and an anionic detergent (pH 4.5).

pHisoHex—an emulsion of an anionic detergent, entsulfon, lanolin cholesterols, petrolatum, and hexachlorophene (pH 5.5).

Hi-Bi-clens-chlorhexidine gluconate plus a sudsing base (pH 5.1 to 6.5).

Tincture of green soap-potassium oleate, isopropanol, potassium coconut oil, soap.

Dakin's solution 0.2 percent solution hypochlorite solution.

Hydrogen peroxide—an oxidizing agent.

Benzalkonium chloride (Zephiran)—a quaternary ammonium compound that works as a cationic surface active agent.

Nonionic surfactants-Pluronic F-68 (Shur-Clens) and Poloxamer-188 (Pharma Clens)-agents that have no antimicrobial activity (pH 7.1).

The use of chlorhexidine is particularly advantageous because it is broad spectrum, binds to the skin (to provide residual activity), works rapidly and, when used according to the subject invention, is non-toxic.

Chlorhexidine is a chemical antiseptic, that can be used to combat both gram positive and gram negative microbes. It is both bacteriostatic and bactericidal. Various species of bacteria are involved in the pathogenesis of wound infection and/or secondarly cellulitis. At times these infections can result in disfigurement, loss of extremities, prolonged convalences, and/or death. The therapeutic effects of irrigation solution of the subject invention is to combat microbes typically involved in the pathology of these infections by its antiseptic properties and those associated with the irrigation process itself. Controlling the microbial load in wounds is a vital factor in minimizing infection and thus decreasing and/or preventing disease.

Spectrum of Activity

Chlorhexidine is active against aerobic and anaerobic gram-positive and gram-negative bacteria. The drug also has some activity against *Chlamydia trachomatis*, certain fungi, and certain viruses.

Aerobic Bacteria

Chlorhexidine is highly active against a variety of gram-positive aerobic bacteria, including *Streptococcus mutans, S. pyogenes* (group A β-hemolytic streptococci), *S. salivarius*, and *S. sanguis*. Chlorhexidine is active against *Staphylococcus aureus, S. epidermidis, S. haemolyticus, S. hominis*, and *S. simulans*. The drug is active against both oxacillin-resistant (ORSA) and oxacillin-susceptible staphylococci (also known as methicillin-resistant [MRSA] or methicillin-susceptible staphylococci).

Chlorhexidine is active against *Enterococcus*, including *E. faecalis* and *E. faecium*, and is active against both vancomycin-susceptible and vancomycin-resistant strains.

Anaerobic Bacteria

Chlorhexidine is active against some anaerobic bacteria. The drug is active against some strains of *Bacteroides, Propionibacterium, Clostridium difficile*, and *Selenomonas*, but is less active against *Veillonella*.

Fungi

Chlorhexidine has some activity against *Candida albicans, C. dubliniensis, C. glabrata* (formerly *Torulopsis glabrata*), *C. gullermondii, C. kefyr* (formerly *C. pseudotropicalis*), *C. krusei, C. lusitaniae*, and *C. tropicalis* (formerly *C. parapsilosis*). Chlorhexidine also has some activity against dermatophytes, including *Epidermophyton floccosum, Microsporum gypseum, M. canis*, and *Trichophyton mentagrophytes*.

Viruses

Chlorhexidine appears to have antiviral activity against viruses that have a lipid component in their outer coat or have an outer envelope such as cytomegalovirus (CMV), human immunodeficiency virus (HIV), herpes simplex virus types 1 (HSV-1) and 2 (HSV-2), influenza virus, parainfluenza virus, and variola virus (smallpox virus).

Methods and Formulations

Advantageously, because the methods of the subject invention can be used to accurately and efficiently deliver an active ingredient to a target site in a patient, it is possible, in certain embodiments, to utilize reduced concentrations of active ingredients. Thus, in one embodiment of the subject invention, a low concentration solution of chlorhexidine can be used to effectively reduce infections at, for example, a wound, surgical site, or other tissue opening. In a preferred embodiment, the chlorhexidine solution is less than 4%. In a more preferred embodiment the chlorhexidine is less than 2%, or even less than 1%. In one embodiment, the chlorhexidine solution is 0.05%. In a further embodiment, the chlorhexidine solution is between 0.02% and 0.05%. Specifically exemplified herein is the use of chlorhexidine gluconate.

As described above, in one embodiment of the subject invention, the device of the subject invention is used to deliver an active agent, such as an antimicrobial agent, to a target site, such as a wound. Subsequent to the administration of the active agent, the site can then be flushed with, for example, saline to remove at least any excess of the active agent. Preferably, this flushing occurs within five minutes of the administration of the chlorhexidine solution. More preferably, this flushing occurs within one to three minutes of the administration of the chlorhexidine solution. In this way, any potential toxicity associated with the active agent can be reduced or eliminated. In the case of chlorhexidine gluconate, rinsing with an irrigation fluid removes excess chlorhexidine that has not bound to, for example, proteins of the skin.

In yet another embodiment, a diagnostic agent can be administered using the device and method of the subject invention. The diagnostic agent may be, for example, an antibody, protein, or polynucleotide that binds to a target biomolecule. Any such binding may then be visualized utilizing technologies known to those skilled in the art. These technologies include, for example, the use of fluorophores or other labels that can be visualized either by the naked eye or through appropriate detection instruments. The diagnostic applications of the subject invention include the detection of bacteria, viruses, parasites and other pathogens. Cancer cells can also be visualized using the diagnostic methods of the subject invention.

In yet another embodiment, the device and method can be used to deliver growth factors and/or protease inhibitors to a target site. Such growth factors and/or protease inhibitors, which can, for example, expedite the healing of wounds, are well known to those skilled in the art.

In yet another embodiment, the method of the subject invention can be used to deliver oxygenated water and/or "enhanced water" to a target site. The enhanced water can be that which is described in, for example, published U.S. Patent Application 20050191364 and the references cited therein (all of which are incorporated herein by reference in their entireties). The use of the subject method for the effective delivery of such oxygenated or enhanced water can be used to promote tissue healing and reduce infections.

In a further embodiment, the device and method of the subject invention can be used to efficiently deliver anti-microbial peptides (AMPs) to a target site. AMPs are well known in the art. Antimicrobial peptides are predominantly small polypeptides that inhibit the growth of microbes. As effectors of innate immunity, antimicrobial peptides directly kill a broad spectrum of bacteria, fungi, and viruses. In addition, these peptides modify the local inflammatory response and activate mechanisms of cellular and adaptive immunity. Cathelicidins and defensins comprise the major families of AMPs in the skin, although other cutaneous peptides, such as proteinase inhibitors, chemokines, and neuropeptides, also demonstrate antimicrobial activity. See, for example, Braff, M. et al., (2005) "Cutaneous Defense Mechanisms by Antimicrobial Peptides," *J Invest Dermatol,* 125:9-13.

The Drug Delivery Device

In one embodiment, the subject invention provides a reservoir housing containing a solution with one or more active agents, wherein the reservoir housing has attached to it a discharge means having a plurality of ports through which a sufficient volume of the solution can pass at an appropriate pressure for effective delivery of the solution, including the active agent, to a target site.

FIG. 1 shows an embodiment of the subject invention wherein the device comprises a squeezable reservoir housing having a wall 60 that forms a reservoir that can contain therein an irrigation material including a medicinal agent. The reservoir housing has a mouth 62, which communicates the reservoir to the outside of the housing. Disposed over the reservoir housing mouth, and affixed to the reservoir housing mouth is a discharge means 80, 100.

In a preferred embodiment, the nozzle(s) of the current invention are specifically designed to reduce the pressure loss as the fluid leaves the reservoir housing.

In a preferred embodiment, each nozzle acts as a jet through which fluid is forced, under pressure, to achieve velocities and pressures appropriate for efficient irrigation. The nozzles are designed to reduce friction and turbulence and facilitate achieving sufficient irrigation pressures with minimal operator effort.

Figure 3:
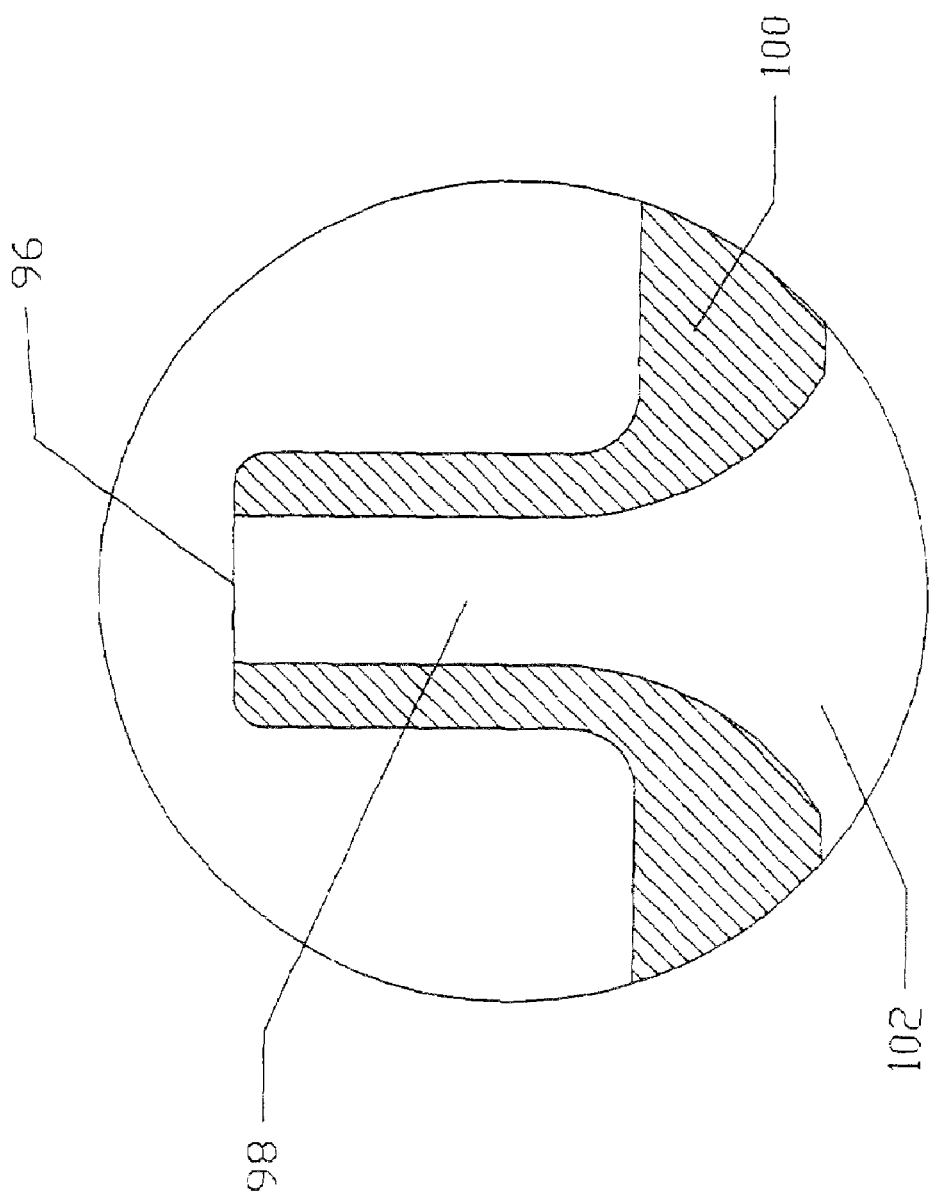
FIG. 3 shows a cross-sectional view of a port of the subject invention.

In certain embodiments of the invention, the nozzle is a "shaped" nozzle defined by a shaped passageway (see FIGS. 2 and 3). As used herein, the "shaped passageway" extends the length of the nozzle and is defined by a cylindrical bore 98 that narrows as it approaches the outlet port 96. The shaped passageway of the nozzle limits the generation of turbulence in the irrigation fluid as it passes through the nozzle(s) during the operation of the wound irrigation device of the subject invention. Therefore, fluid passing through the nozzle experiences laminar flow (or at least a reduction in turbulence) as it passes through and exits the nozzle. Thus, as used herein, reference to the "shaped passageway" refers to a nozzle with a passageway where the cross-sectional area of the inlet port 102 is greater than the cross-sectional area at or near the outlet port 96 wherein the inlet port is curved (not squared off), and the turbulence through the nozzle is less than the turbulence of a nozzle of the same or similar size but having a "squared-off" inlet port and/or constant diameter passageway. This shaped nozzle has been found to be particularly advantageous for achieving desired irrigation fluid pressures and velocities according to the subject invention. The description of nozzles set forth in WO 2005/030297 is incorporated herein in its entirety by reference.

The nozzle passage area 98 is preferably defined by a funnel shape having a portion with a curved surface, where the nozzle cross-section decreases from an upstream wider end 102 to the downstream end 96.

FIG. 2 shows a specific embodiment of the elongated, shaped nozzles of the subject invention. In FIG. 2 the conical shaped nozzle is 0.2 inches long (from inlet port to outlet port).

As would be appreciated by a person skilled in the art having the benefit of the current disclosure, the nozzles of the subject invention can be formed within the material of the discharge means. Thus, if the discharge means is formed of plastic that is sufficiently thick, then the nozzles may simply pass through the material of the discharge means. Alternatively, the nozzles may extend from either side of the discharge means.

In certain embodiments, the discharge means is detachably affixed to the reservoir housing mouth. In such embodiments, the reservoir mouth can include connecting means such as threads, snap fits, grooves, or other mechanical connection configurations for operably connecting the reservoir housing mouth to the discharge means.

The wall of the reservoir housing can be made or molded from any material that is preferably rigid enough to stand upright when the reservoir is filled with irrigation solution. In a typical embodiment, the reservoir housing is formed by a molded plastic, which is pliable enough so that the wall of the reservoir housing can be squeezed or compressed by hand to exert pressure on the contents of the reservoir. The preferred embodiment comprises a plastic material that is pliable enough to squeeze by hand and which also has sufficient resilience to return to its original shape when no longer compressed or squeezed. In a preferred embodiment, this return to the original shape happens very quickly.

The horizontal cross-sectional shape of the reservoir housing can be circular, square, rectangular, or other geometric shapes as desired or as already available. The walls can be tapering toward one end or the other. Alternatively, other shapes can be made for the reservoir housing according to and adapted for a particular use. For example, part of the reservoir housing wall can be slightly rounded as in a general hourglass shape and/or can be molded for ergonomics to easily fit a hand or otherwise to facilitate handling or compressing the reservoir housing. The reservoir formed by the housing of the subject invention can typically hold a volume of about 100 ml to 1000 ml, preferably about 250 ml to about 750 ml and most preferably about 500 ml. Advantageously, with manual compression, the device and method of the subject invention can deliver 500 ml of irrigation fluid in less than 30 seconds and, typically, in 15 to 25 seconds. The fluid is delivered at about 4 to 20 psi. Lower pressures can be used for irrigating eye wounds. For irrigation of wounds in or around the eye, a pressure of about 1 psi to about 5 psi is preferred.

Further, in a preferred embodiment, the reservoir housing comprises at one end a neck portion formed at the mouth of the reservoir housing. The neck portion of the reservoir housing is generally at least slightly smaller in cross sectional area than the reservoir housing. The reservoir housing neck is preferably integrally molded with the reservoir housing, but can be formed or molded separately and affixed to the mouth of the reservoir housing. The material used for the neck portion of the reservoir housing can be the same as the material used to make the reservoir housing cylinder. Alternatively, the neck portion can be a different material, for example, a more rigid or sturdy material than the compressible material forming the reservoir housing wall. For example, the material used to make the neck portion can be a metal or a hard plastic, or the like.

With reservoir housing embodiments that include a neck portion, the discharge means is typically disposed over and affixed to the neck portion. In a related embodiment, the neck portion of the reservoir housing can include a connecting means for detachably affixing a discharge means thereto. The connecting means can include threads, latches, grooves, or other mechanical connection configurations for operably connecting the neck portion to the discharge means. The connecting means can be on the outer face of the neck portion, forming a male connecting end, or can be on the inner face forming a female connecting end of the neck portion.

In a preferred embodiment, the discharge means has a plurality of nozzles 70 whereby the irrigation solution in the reservoir passes through in a pressurized and directional manner. A backsplash shield 90 can also be provided either with the reservoir housing or with the discharge means.

The back-splash protective shield protects the health care professional (or other user) from back-splash of human and or animal body fluids that are mixed with and splashed from the wound when the wound is contacted by the discharged irrigation solution.

As used herein, reference to a "dispersed" stream of solution means that the area from which the stream emanates, or the area which it contacts, is larger than that which can be achieved using a typical syringe for irrigation. A typical syringe, as is well known in the art can be, for example, a 16 or 18 gauge syringe. In one embodiment, the dispersed stream can be achieved using multiple nozzles. The nozzles can be presented in a variety of patterns on a discharge means, such as a circular or square pattern.

In certain embodiments, the discharge means is designed with connecting means that are threads or grooves, which allow for complementary attachment to currently available irrigation solution bottles. Thus, the discharge means of the subject invention can be interchangeable, when desired, with the screw-cap that is provided with an irrigation solution bottle as are available. The screw-top design of the discharge means provides the operator with the option of using the reservoir housing with the nozzles of the invention or to threadably remove the discharge means and pour out or change the irrigation solution.

Each of the nozzles of the discharge means can be of any desirable size, preferably less than one-eighth inch in diameter and having a size between about a 10 gauge hypodermic needle and about a 30 gauge needle, and most preferably having a size ranging from that of a 16 gauge needle to a 25 gauge needle. Specific dimensions and shapes are shown in FIG. 2. The outlet port 96 may have, for example, an inner diameter of about 0.02 to about 0.07 inches. For the venturi shaped nozzle (FIG. 3), the diameter of the inlet port 102 (proximal to the reservoir) can be, for example, from about 0.05 to about 0.30 inches, or more.

Each of the nozzles can be the same size or the nozzles can be different sizes and shapes. The different sizes of nozzles allow for the liquid to be expelled from the discharge means at different pressures. For example, the 16 gauge nozzle allows for a stream having about 6 psi pressure when the device is squeezed by the normal adult; the 25 gauge nozzle provides a pressure of up to about 20 psi from each nozzle.

The shaped nozzles of the invention have the added advantage when compared to other nozzles in that little or no release of irrigation material is permitted without pressure being applied to the irrigation material. For example, if a reservoir housing with shaped nozzles is tipped onto its side or even held upside-down with gravitational pull on the irrigation material through the discharge means, there will be little or no release of irrigation material through the shaped nozzles.

In a preferred embodiment, the discharge means 70 comprises four nozzles. Additionally, to discharge the irrigation solution at appropriate pressure, the diameter of the nozzles can be about 0.02 to 0.07 inches in diameter.

From the description of the device herein above, a method of using the subject device would readily be understood and adaptable by those persons having ordinary skill in the art. The reservoir housing and contents can be stored in a sterile environment, e.g., sterile packaging which is opened immediately prior to use. The reservoir housing can be directed towards the wound and squeezed or compressed to expel or discharge the solution in the desired direction, and at the desired pressure to effect irrigation of a wound to remove contaminants or debris and to deliver the active agent(s). See also the Example 1, provided below.

It would also be understood that the described discharge means can be packaged separately from the reservoir housing. The discharge means is packaged in a sterile environment. In one embodiment, the drug delivery device is provided in a sterile laceration tray. According to the subject invention, the laceration tray has, in addition to the drug delivery device of the subject invention, other items conveniently provided for treating wounds. Contemplated items that can be included in a laceration tray include, but are not limited to, needle holders (i.e., 5" floor-grade smooth); scissors (i.e., 4.5" floor-grade straight Iris scissors); hemostats (i.e., 5" floor-grade curved mosquito hemostat); forceps (i.e., floor-grade tissue forceps with 1×2 teeth); cups (i.e., 2 oz. medicine cups); syringes (i.e., 10 cc Luer Lock syringe); needles (i.e., 25 gauge×⅝" needle; 27 gauge×1.5" needle; 18 gauge×1.5" needle); dressings (i.e., gauze dressings); drapes (i.e., polylined fenestrated drapes); and towels (i.e., absorbent towels).

In a method of use, where a reservoir housing 60 having discharge means 70 affixed thereto is provided. The discharge means 70 is directed towards the wound, and the reservoir housing 60 is compressed, discharging the irrigation solution through the discharge means 70. The solution can be discharged at a range of pressures of about 4-20 lbs/in$^2$, with a preferred pressure of about 7 psi.

The reservoir housing 60 can be compressed manually or via other mechanical means. For example, the operator may compress the reservoir housing either one hand or two hands, to provide increased pressure (i.e., 16 psi). Alternatively, a pressure means can be activated to generate a dispersed stream of irrigation solution through the discharge means.

In another method of use, where a reservoir housing 60 and discharge means 70 are provided separately, the discharge means is affixed to the mouth or neck portion of the reservoir housing via complementary connecting means. After the discharge means is affixed to the reservoir housing, the discharge means is directed towards the target site, and the reservoir housing is compressed to discharge a dispersed stream of irrigation solution through the nozzles of the discharge means.

Significantly, it is known that more force is required to rid the wound of particles with a small surface area (e.g., bacteria) than to remove particles with a large surface area (e.g., dirt, sand, or vegetation). Minimum recommended volumes of irrigation solution vary, but for a moderately sized potentially contaminated wound, for example a laceration 3-6 cm long and less than 2 cm deep, at least 200 to 500 ml, or more should be used. Greater volumes, on the order of one to two liters, may be required for larger or heavily contaminated wounds. Irrigation should continue at least until all visible, loose particulate matter has been removed.

Following is an example that illustrates procedures for practicing the invention. This example should not be construed as limiting.

EXAMPLE 1

Methods of Irrigation

When a patient presents a wound to a medical or other health care professional skilled in the art, that medical professional assesses the extent of the injury sustained by the patient, including all other life threatening injuries. Appropriate action regarding these life threatening injuries is performed and a history is recorded. All wounds are covered to minimize further contamination until the actual repair process begins.

For examination of the wound, it is assumed that a medical professional would have performed a detailed evaluation of the extent of tissue injury, including but not limited to: anatomical area considerations, depth of the wound, type of injury, e.g., crash injury, puncture wound, bites, missiles, cuts with sharp objects, or the like. Included in this examination would be a determination of the type(s) of contamination, time elapsed between the occurrence of the injury to presentation, gross contamination of a wound, and other medical factors associated with an increase incidence of infection (for example, diabetics, AIDS patients, and chemotherapeutics patients).

The wound and surrounding tissue, at the option of the health care professional, could be anesthetized using topical, local, or general anesthetics before the wound-cleansing method begins. Alternatively, an anesthetic may be delivered using the device and method of the subject invention.

In one embodiment, the subject device has a discharge means affixed to a reservoir housing. The subject device can be held in either hand as preferred by the user. Normally, it would be held in the dominant hand in a bottle-holding fashion. This allows the medical care professional to gently open the wound if needed, with the opposite hand, preferably protected by a sterile glove, to expose the depths of the wound.

Once the depths of the wound have been exposed, the end of the reservoir housing having the discharge means affixed thereto is directed towards the wound. Manual or mechanically produced pressure is applied to the reservoir housing to expel the irrigation solution with active agent through the nozzles of the discharge means. The wound should be irrigated in this fashion until all visible evidence of contamination has been removed. A potentially contaminated wound of any size should be irrigated with a minimum of 200-300 ml of irrigation solution. Heavily contaminated or larger wounds may require 2-3 liters of irrigation solution. The health care professional could vary the angle of the discharged irrigation solution from the discharge means in reference to the wound to further assist with the dislodgement of contaminants.

Following an initial irrigation of the wound, a re-examination of the wound should be undertaken. The wound should be explored to its base to ascertain that no visible foreign bodies or contaminants remain. If foreign bodies or contaminants are found, the irrigation process should be repeated followed by a re-examination. This may continue for several cycles.

Once irrigation has been completed, i.e., no visible contaminants remain, the damaged tissue would be repaired in a standard accepted fashion.

Irrigation of skin wounds such as cuts, scrapes, punctures, abrasions, etc. are particular well-suited for irrigation according to the subject invention.

EXAMPLE 2

Routes of Administration

Table 1 provides a listing of various routes of administration that can be used according to the subject invention.

TABLE 1

Routes of Administration

| Delivery Route | Description |
| --- | --- |
| AURICULAR (OTIC) | Administration to or by way of the ear. |
| BUCCAL | Administration directed toward the cheek, generally from within the mouth. |
| CONJUNCTIVAL | Administration to the conjunctiva, the delicate membrane that lines the eyelids and covers the exposed surface of the eyeball. |
| CUTANEOUS | Administration to the skin. |
| DENTAL | Administration to a tooth or teeth. |
| ENDOCERVICAL | Administration within the canal of the cervix uteri. Synonymous with the term intracervical.. |
| ENDOSINUSIAL | Administration within the nasal sinuses of the head. |
| ENDOTRACHEAL | Administration directly into the trachea. |
| ENTERAL | Administration directly into the intestines. |
| EPIDURAL | Administration upon or over the dura mater. |
| EXTRA-AMNIOTIC | Administration to the outside of the membrane enveloping the fetus |
| EXTRACORPOREAL | Administration outside of the body. |
| INFILTRATION | Administration that results in substances passing into tissue spaces or into cells. |
| INTERSTITIAL | Administration to or in the interstices of a tissue. |
| INTRA-ABDOMINAL | Administration within the abdomen. |
| INTRA-ARTICULAR | Administration within a joint. |
| INTRABILIARY | Administration within the bile, bile ducts or gallbladder. |
| INTRABRONCHIAL | Administration within a bronchus. |
| INTRACARDIAC | Administration with the heart. |
| INTRACARTILAGINOUS | Administration within a cartilage; endochondral. |
| INTRACAVERNOUS | Administration within a pathologic cavity, such as occurs in the lung in tuberculosis. |
| INTRACAVITARY | Administration within a non-pathologic cavity, such as that of the cervix, uterus, or penis, or such as that which is formed as the result of a wound. |
| INTRACEREBRAL | Administration within the cerebrum. |
| INTRACORPORUS CAVERNOSUM | Administration within the dilatable spaces of the corporus cavernosa of the penis. |
| INTRADUCTAL | Administration within the duct of a gland. |
| INTRADUODENAL | Administration within the duodenum. |
| INTRADURAL | Administration within or beneath the dura. |
| INTRAESOPHAGEAL | Administration within the esophagus. |
| INTRAGASTRIC | Administration within the stomach. |
| INTRAILEAL | Administration within the distal portion of the small intestine, from the jejunum to the cecum. |
| INTRALESIONAL | Administration within or introduced directly into a localized lesion. |
| INTRALUMINAL | Administration within the lumen of a tube. |
| INTRALYMPHATIC | Administration within the lymph. |
| INTRAMEDULLARY | Administration within the marrow cavity of a bone. |
| INTRAMENINGEAL | Administration within the meninges (the three membranes that envelope the brain and spinal cord). |
| INTRAOCULAR | Administration within the eye. |
| INTRAOVARIAN | Administration within the ovary. |

TABLE 1-continued

Routes of Administration

| Delivery Route | Description |
| --- | --- |
| INTRAPERICARDIAL | Administration within the pericardium. |
| INTRAPERITONEAL | Administration within the peritoneal cavity. |
| INTRAPLEURAL | Administration within the pleura. |
| INTRAPROSTATIC | Administration within the prostate gland. |
| INTRAPULMONARY | Administration within the lungs or its bronchi. |
| INTRASINAL | Administration within the nasal or periorbital sinuses. |
| INTRASPINAL | Administration within the vertebral column. |
| INTRASYNOVIAL | Administration within the synovial cavity of a joint. |
| INTRATENDINOUS | Administration within a tendon. |
| INTRATESTICULAR | Administration within the testicle. |
| INTRATHECAL | Administration within the cerebrospinal fluid at any level of the cerebrospinal axis, including injection into the cerebral ventricles. |
| INTRATHORACIC | Administration within the thorax (internal to the ribs); synonymous with the term endothoracic. |
| INTRATUBULAR | Administration within the tubules of an organ. |
| INTRATUMOR | Administration within a tumor. |
| INTRATYMPANIC | Administration within the aurus media. |
| INTRAUTERINE | Administration within the uterus. |
| INTRAVESICAL | Administration within the bladder. |
| INTRAVITREAL | Administration within the vitreous body of the eye. |
| IRRIGATION | Administration to bathe or flush open wounds or body cavities. |
| LARYNGEAL | Administration directly upon the larynx. |
| NASAL | Administration to the nose; administered by way of the nose. |
| NASOGASTRIC | Administration through the nose and into the stomach, usually by means of a tube. |
| OCCLUSIVE DRESSING TECHNIQUE | Administration by the topical route which is then covered by a dressing which occludes the area. |
| OPHTHALMIC | Administration to the external eye. |
| ORAL | Administration to or by way of the mouth. |
| OROPHARYNGEAL | Administration directly to the mouth and pharynx. |
| PERCUTANEOUS | Administration through the skin. |
| PERIARTICULAR | Administration around a joint. |
| PERIDURAL | Administration to the outside of the dura mater of the spinal cord.. |
| PERINEURAL | Administration surrounding a nerve or nerves. |
| PERIODONTAL | Administration around a tooth. |
| RECTAL | Administration to the rectum. |
| RESPIRATORY (INHALATION) | Administration within the respiratory tract by inhaling orally or nasally for local or systemic effect. |
| RETROBULBAR | Administration behind the pons or behind the eyeball. |
| SOFT TISSUE | Administration into any soft tissue. |
| SUBARACHNOID | Administration beneath the arachnoid. |
| SUBCONJUNCTIVAL | Administration beneath the conjunctiva. |
| SUBCUTANEOUS | Administration beneath the skin; hypodermic. Synonymous with the term SUBDERMAL. |
| SUBLINGUAL | Administration beneath the tongue. |
| SUBMUCOSAL | Administration beneath the mucous membrane. |
| TOPICAL | Administration to a particular spot on the outer surface of the body. The E2B term TRANSMAMMARY is a subset of the term. |
| TRANSMUCOSAL | Administration across the mucosa. |
| TRANSPLACENTAL | Administration through or across the placenta. |
| TRANSTRACHEAL | Administration through the wall of the trachea. |
| TRANSTYMPANIC | Administration across or through the tympanic cavity. |
| URETERAL | Administration into the ureter. |
| URETHRAL | Administration into the urethra. |
| VAGINAL | Administration into the vagina. |

It should be understood that the example and embodiment described herein is for illustrative purposes only and that various modifications or changes in light thereof will be suggested to persons skilled in the art and are to be included within the spirit and purview of this application and the scope of the appended claims.

I claim:

1. A wound irrigation device comprising a reservoir housing, containing a sterile aqueous wound irrigation solution that comprises an antiseptic agent, wherein said wound irrigation device comprises a discharge means that directs a stream of said wound irrigation solution when said reservoir housing is compressed, wherein said reservoir housing is made of a resilient compressible material, and wherein said antiseptic agent consists of chlorhexidine that is present at a concentration of 1% or less.

2. The wound irrigation device, according to claim 1, which contains from 250 ml to 750 ml of wound irrigation solution.

3. The wound irrigation device according to claim 1, wherein said device further comprises a backsplash shield.

4. The device, according to claim 1, wherein the biologically active agent is chlorhexidine at a concentration of 0.05% or less.

5. The device, according to claim 1, wherein the chlorhexidine is in the form of chlorhexidine gluconate.

6. The device, according to claim 1, wherein the pH of the irrigation solution is between pH 5.5 and pH 7.0.

7. The device, according to claim 1, wherein the chlorhexidine is at a concentration of about 0.05%.

8. The device, according to claim 1, wherein said wound irrigation fluid consists of sterile water and chlorhexidine at a concentration of about 0.05%.

* * * * *